United States Patent
Denny et al.

(10) Patent No.: US 6,251,933 B1
(45) Date of Patent: Jun. 26, 2001

(54) SECO PRECURSORS OF CYCLOPROPYLINDOLINES AND THEIR USE AS PRODRUGS

(75) Inventors: William Alexander Denny; Moana Tercel; Graham John Atwell, all of Auckland (NZ); Jared Milbank, Rochester, NY (US)

(73) Assignee: The Cancer Research Campaign Technology Limited, London (GB)

( * ) Notice: Subject to any disclaimer, the term of this patent is extended or adjusted under 35 U.S.C. 154(b) by 0 days.

(21) Appl. No.: 09/319,771

(22) PCT Filed: Dec. 12, 1997

(86) PCT No.: PCT/NZ97/00166

§ 371 Date: Jun. 11, 1999

§ 102(e) Date: Jun. 11, 1999

(87) PCT Pub. No.: WO98/25898

PCT Pub. Date: Jun. 18, 1998

(51) Int. Cl.[7] ............ A61K 31/404; C07D 209/02; A61N 31/12; A61N 35/00
(52) U.S. Cl. .................. 514/414; 548/465; 534/703
(58) Field of Search .................. 548/491, 465; 514/414

(56) References Cited

FOREIGN PATENT DOCUMENTS 0154445  9/1985  (EP) .

(List continued on next page.)

OTHER PUBLICATIONS

Boger et al.; *Tetrahedron*; (1991) 47 (14/15):2661–2682.

(List continued on next page.)

Primary Examiner—Floyd D. Higel
Assistant Examiner—Ebenezer Sackey

(74) Attorney, Agent, or Firm—Pamela J. Sherwood; Bozicevic, Field & Francis LLP

(57) ABSTRACT

A compound which is a 6-substituted seco indoline of the formula (I):

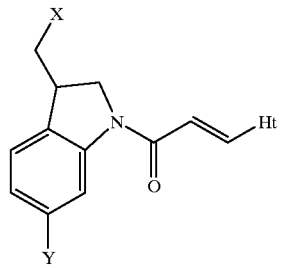

(I)

wherein:

X is halogen or $OSO_2R$ where R represents H or $C_{1-5}$ alkyl optionally substituted with from 1 to 4 hydroxyl, acid (COOH) or amino groups which amino may be optionally substituted by one or two $C_{1-5}$ alkyl groups;

Y is $NO_2$, $N_3$, NHOH, NHR, NRR, N=NR, N(O)RR, SR or SSR, where R is defined as above, but that in the case where Y is SSR or N=NR, then R can also be another moiety of formula (I);

or Y is a group of formula:

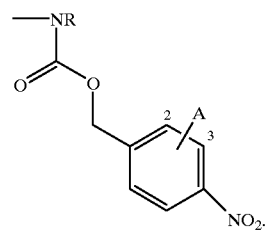

(II)

14 Claims, 2 Drawing Sheets

SCHEME 1

FOREIGN PATENT DOCUMENTS

| | | |
|---|---|---|
| 0461603 | 12/1991 | (EP) . |
| 0520435 | 12/1992 | (EP) . |
| WO 88/07378 | 10/1988 | (WO) . |

OTHER PUBLICATIONS

Boger et al.; *J. Org. Chem.*; (1990) 55:4499–4502.

Boger et al.; *J. Am. Chem. Soc.*; (1990) 112:8961–8971.

Chemical Abstracts, vol. 126, No. 6, (Feb. 10, 1997), abstract No. 69799.

Chemical Abstracts, vol. 126, No. 6, (Feb. 10, 1997), abstract No. 74710.

SCHEME 1

SCHEME 2

SECO PRECURSORS OF CYCLOPROPYLINDOLINES AND THEIR USE AS PRODRUGS

This application is a 371 of PCT/NZ97/00166 filed Dec. 12, 1997.

The present invention relates to novel amino analogues of the general class of cyclopropylindoles and their seco precursors, and is particularly concerned with the use of these compounds as prodrugs for antibody-directed enzyme-prodrug therapy (ADEPT) and gene-directed enzyme-prodrug therapy (GDEPT) for cancer.

BACKGROUND TO THE INVENTION

The use of prodrugs represents a clinically very valuable concept in cancer therapy since, particularly where the prodrug is to be converted to an anti-tumour agent under the influence of an enzyme that is linkable to a monoclonal antibody that will bind to a tumour associated antigen, the combination of such a prodrug with such an enzyme monoclonal/antibody conjugate represents a very powerful clinical agent. This approach to cancer therapy, often referred to as "antibody directed enzyme/prodrug therapy" (ADEPT) is disclosed in WO88/07378.

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al, Proc. Natl. Acad. Sci. USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French, Annu. Rev. Biochem., 1993, 62;191. The term "GDEPT" (gene-directed enzyme prodrug therapy) is used to include both viral and non-viral delivery systems.

Cyclopropylindole compounds are a class of highly potent antitumour antibiotics with the natural products CC-1065 (V. L. Reynolds et al, J. Antibiot., 39, 1986, 319–334) and the duocarmycins (D. L. Boger, Pure & Appl. Chem., 66, 1994, 837–844), having $IC_{50}$'s in the low pM range. These compounds bind in the minor groove of DNA and alkylate in a highly sequence selective manner at N-3 of adenine (D. L. Boger et al, Tetrahedron, 47, 1991 2661–2682). Studies with compounds that model the alkylation subunit have shown that the more stable open chain seco precursors are as potent as the cyclopropylindole compounds. Further, ring closure is not essential for DNA alkylation, and there is some measure of electronic control by the both the 6-substituent (D. L. Boger et al, J. Am. Chem. Soc., 113, 1991, 3980–3983) and the 1-substituent (D. L. Boger and W. Yun, J. Am. Chem. Soc., 116, 1994, 5523–5524) on the rate of alkylation.

A number of synthetic analogues of the natural products have been prepared in which the oxygen at the 6-position is protected as a carbamate that must be cleaved (by non-specific enzymatic hydrolysis) for activity. These compounds include carzelesin (L. H. Li et al, Cancer Res., 52, 1992, 4904–4913) and KW-2189 (E. Kobayashi et al, Cancer Res., 54, 1994, 2404–2410) which show anticancer activity against a range of human tumours and are in clinical trial. These compounds have the structures A and B respectively:

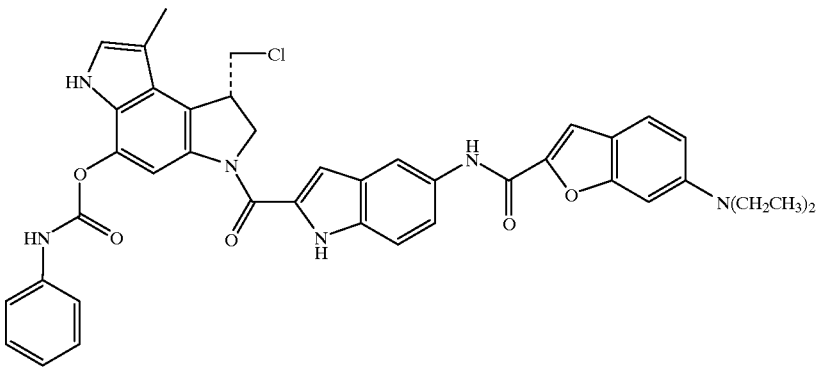

(A)

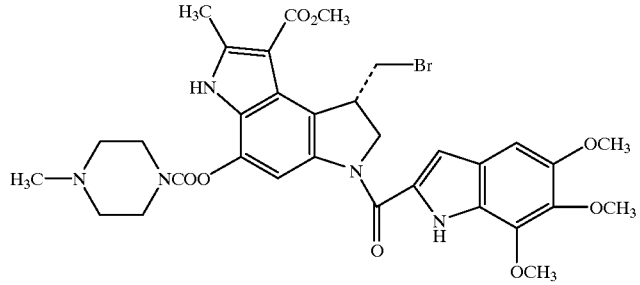

(B)

Further analogues of a similar type are disclosed in WO88/04659 and WO91/16324.

i.: $Ph_3P=CHCOOMe$/benzene/reflux/24 h.
ii: Malonic acid/piperidine/pyridine/20° C./20 h.
iii: Dimethyl sulfate/$NaHCO_3$/aqueous MeOH/reflux/1 h.
iv: $Fe/(BuCO)_2O$/aqueous MeOH/reflux/45 min.
v: NaOH/aqueous MeOH/reflux/50 min.
vi: EDCI.HCl/DMF/40° C./16 h.
vii: Fe/AcOH/MeOH/water/reflux/40 min.
viii: $4-NO_2C_6H_4CH_2OCOCl$/pyridine/20° C./1.5 h.

Figure 2:
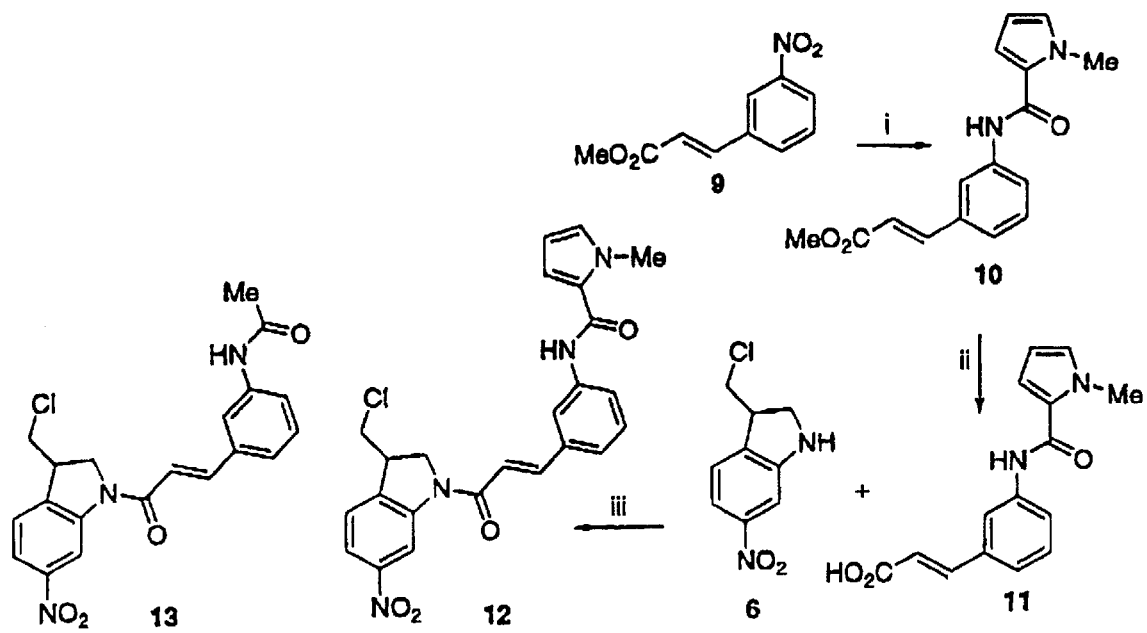

FIG. 2 shows Scheme 2. The steps (i) to (iii) involve the following reactants/conditions:

i: 1-Mepyrrole-2-carboxylic acid/EDCI.HCl/pyridine/50° C. 2.5 h.
ii: $Cs_2CO_3$/aqueous MeOH/reflux/2.5 h.
iii: EDCI.HCl/DMA/20° C./2 h.

DISCLOSURE OF THE INVENTION

In one aspect, the present invention relates to the new class of 6-substituted seco indolines, represented by formula (I):

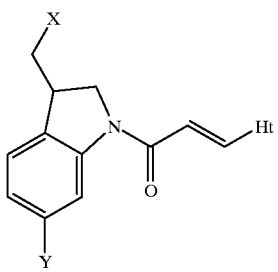

(I)

wherein:

X is halogen or $OSO_2R$, where R represents H or lower alkyl (up to five carbon atoms) optionally substituted with from 1 to 4 hydroxyl, acid (COOH) or amino groups which amino may be optionally substituted by one or two lower alkyl groups;

Y is $NO_2$, $N_3$, NHOH, NHR, NRR, N=NR, N(O)RR, SR or SSR, where R is defined as above, but that in the case where Y is N=NR or SSR, then R can also be another moiety of formula (I) (i.e. a or symmetrical disulfide or AZO compound);

or Y is a group of formula:

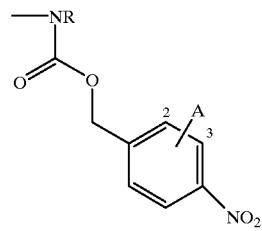

(II)

where R is as defined above, and A may be a group CONHR, NHCOR or OR where R is as defined above at any one of positions 2 or 3;

Ht is a 5 or 6 membered carbocycle or heterocycle containing up to two atoms selected from N, O or S, the carbocycle or heterocycle being optionally substituted by a group Q wherein either Q is one or two of H, OR or NRR where R is defined as above (which may be the same or different when Q is two) or Q is a group $CONHJ^1$, $NHCOJ^1$, $NHCOOJ^1$ or $NHCONHJ^1$ where $J^1$ is either a group R as defined above or a 5 or 6 membered carbocycle or heterocycle containing up to two atoms selected from N, O or S and can bear a substituent R, OR, NHCOR, NHCOOR or NHCONHR where R is as defined above;

or a physiologically functional derivative thereof.

It is recognised that compounds of formula (I) may exist in one of two different enantiomeric forms. In such cases it is to be understood that formula (I) represents either enantiomeric form or a mixture of both.

A halogen group means a fluoro, chloro, bromo or iodo group. A chloro group is preferred. Preferred compounds of formulae (I) include those in which X represents Cl.

Examples of the group Ht include the carbocycle phenyl and the heterocycles pyrrolyl, imidazolyl, pyrazolyl, pyridyl, pyrazinyl, furyl, isothiazolyl, thienyl and morpholinyl. It is preferred that Ht be phenyl or pyrrolyl, e.g. pyrrol-2-yl.

Preferred examples of the group Q include NHCOR where R is $C_{1-4}$ alkyl and $NHCOJ^1$ where $J^1$ is a heterocycle as defined above, and preferably pyrrol-2-yl, optionally substituted on the nitrogen atom by $C_{1-4}$ alkyl.

In another aspect, the present invention relates to the use of the compounds of formula (I) as anticancer drugs. The compounds may be used for the selective killing of oxic and hypoxic tumour cells in methods of treatment of cancers, for example leukemias and particularly solid cancers including breast, bowel and lung tumours, including small cell lung carcinoma.

In a further aspect, the present invention relates to the use of the compounds in which Y is a group of formula (II), in conjunction with nitroreductase enzyme (for example, isolated from E. coli) in methods of ADEPT and GDEPT therapy. Compounds of the formula (I) in which Y is $NO_2$ or N(O)RR may also be used in conjunction with nitroreductase.

The invention also provides pharmaceutical compositions comprising a compound of the formula (I) together with a pharmaceutically acceptable carrier or diluent.

DETAILED DESCRIPTION OF THE INVENTION

In general, compounds of the present invention may be made by reaction of an indoline of formula (IIIa) or (IIIb)

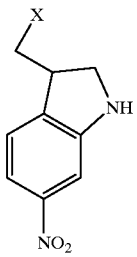

(IIIa)

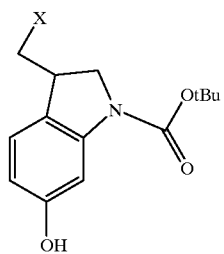

(IIIb)

where X is as defined for formula (I). Compounds of the formula (IIIa) may be reacted with an acid of formula (IV)

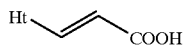

(IV)

where Ht is as defined for formula (I) under conditions suitable for the production of a compound of formula (I).

For example, the reaction may be carried out in a polar aprotic solvent such as DMF or DMA, in the presence of a coupling agent [e.g. 1-(3-dimethylaminopropyl)-3-ethylcarbodiimide hydrochloride].

The compound of formula (I) where Y=$NO_2$ thus obtained may be converted into other compounds of formula (I) by appropriate methods. For example, reduction such as in an alcoholic or aqueous alcoholic solvent with iron powder in the presence of an acid such as acetic acid can be used to prepare compounds of formula (I) where Y=$NH_2$.

Reductive alkylation of componds of formula (I) where Y=$NH_2$ can be used to form compounds of formula (I) in which Y is NHR or NRR. For example, formic/acetic anhydride and diborane gives compounds of formula (I) where Y=NHMe; formaldehyde/sodium cyanoborohydride gives compounds of formula (I) where Y=$NMe_2$.

Controlled hydrogenation of componds of formula (I) where Y=$NH_2$ in e.g. DMF provides the hydroxylamines (Y=NHOH in formula (I)).

Compounds of formula (I) where Y is $NH_2$ may also be prepared by reaction of an indoline formula (IIIb), where X is as defined for formula (I) with an acid such as HCl, and coupling of the product with a compound of formula (IV). Appropriate conditions for the coupling reaction include polar aprotic solvents such as DMF or DMA and a coupling reagent such as 1-(3-dimethylaminopropyl)-3-ethylcarbodiimide hydrochloride (EDCI). Further reaction with: (a) a trifluoromethanesulfonating reagent such as trifluoromethanesulfonic anhydride in the presence of a base (e.g., triethylamine), then; (b) treatment with benzophenone imine, a base such as cesium carbonate, and a palladium or nickel catalyst and appropriate ligand [e.g., palladium acetate and 2,2'-bis(diphenylphosphino)-1,1'-binaphthyl or tetrakis(triphenylphosphine)palladium], then; (c) mild acid cleavage of the resulting imine, using for example HCl or acetic acid in a solvent such as THF-water or THF-MeOH-water mixtures, gives the desired compounds of formula (I) where Y=$NH_2$.

Further compounds of formula (I) where Y=NHR, where R is defined as above, may be prepared by substituting the appropriate amine $H_2NR$ or HNRR for benzophenone imine in the above sequence. The appropriate amines will contain suitably protected forms of the substituents in the R group.

Diazonium chemistry may be used to convert the amino compounds (Y=$NH_2$ in formula (I)) to the azides (Y=$N_3$ in formula (I)), or to sulfur derivatives (Y=SR or SSR in formula (I)).

When Y is a tertiary amine, oxidation (for example with peracids) can be used to provide the corresponding N-oxides (Y=N(O)RR in formula (I)).

Acylation of a compound of formula (I) where Y=NHR with a suitably protected substituted 4-nitrobenzyl derivative of formula (V)

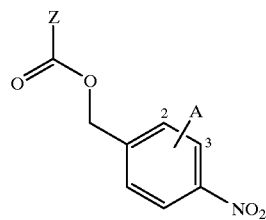

(V)

or reactive derivative thereof, wherein Z is a halogen, particularly chlorine, and A is as defined for formula (II), in the presence of an added base gives the corresponding acyl analogues of general formula (I) where Y is a group of formula (II).

Suitable reaction conditions include presenting the compound of formula (V) in e.g. THEF or dioxane. Suitable bases to be added include $Et_3N$.

Compounds of formulae (IIIa), (IIIb), (IV) and (V) are either commercially available or may be prepared using known starting materials and published chemical methods, and are further illustrated in the Examples. For compounds of formula (IIIb), reference may also be made to D. L. Boger et al, J. Am. Chem. Soc. 1990, 122; 5230–5240.

Compounds of formula (IV), where Q includes a group $J^1$, may be made by reacting a compound of formula (VIa)

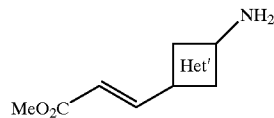

(VIa)

wherein Het' is a 5-or 6-membered carbocycle or heterocycle containing one or two groups N, O or S with a compound of formula $HO_2C$-$J^1$ (or a reactive derivative thereof), or with a compound of formula $H_2N$-$J^1$ or HO-$J^1$ in the presence of phosgene (or a reactive phosgene equivalent). $J^1$ is as defined for formula (I), and can bear suitably protected forms of the substituents as defined above. Other examples of compounds formula (IV) where Q includes a group J¹ may be made by reacting a compound of formula (VIb)

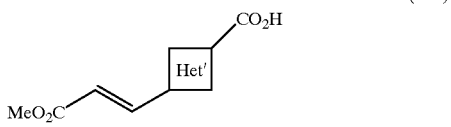

(VIb)

with a compound of formula H₂N-J¹ (or a reactive deriative thereof) wherein Het' and J¹ are as defined above.

The methyl ester group in the resulting compounds which derive from the compounds of formulae (VIa) and (VIb) can then be cleaved under standard conditions to give the free acids.

Figure 1:
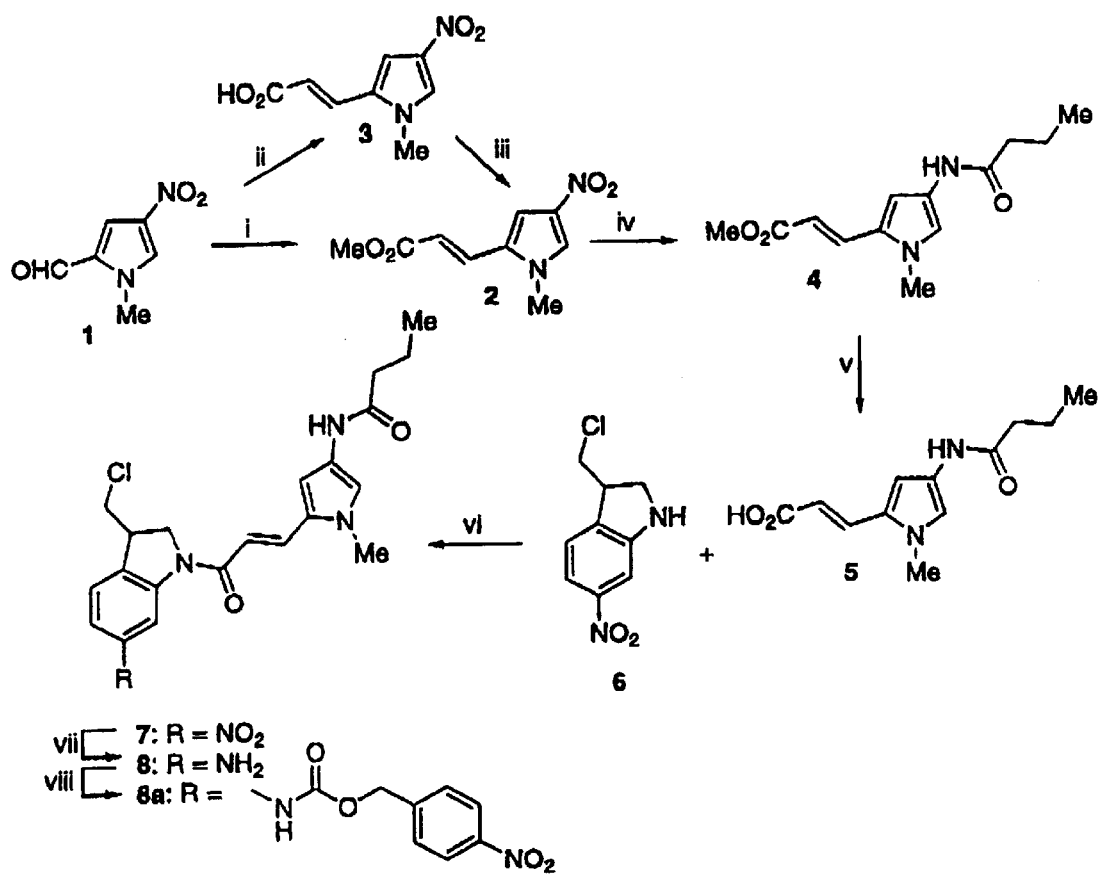
FIG. 1 shows Scheme 1 for the preparation of compounds of the invention. The steps (i) to (vii) involve the following reactants/conditions.

Reference may also be made to Schemes 1 and 2 set out in FIGS. 1 and 2 respectively. Analogous procedures may be used to obtain other compounds of the invention. The compounds of formula (I) can be prepared by the processes outlined for specific examples in Schemes 1 and 2.

In Scheme 1, nitration of commercially available 1-methyl-2-pyrrolecarboxaldehyde as described [P. Fournari, *Bull. Soc. Chem. Fr.,* 1963, 488–491], and crystallisation of the product mixture, gives the 4-nitroaldehyde 1. Wittig reaction of 1 with methyl triphosphorylidene acetate gave the methyl acrylate 2 (which could also be made by a Doebner reaction of 1 with malonic acid to give 3, followed by methylation to 2). Iron dust reduction of 2 in the presence of butyric anhydride gave butyramide 4, which could be hydrolysed to the corresponding acid 5 with aqueous sodium hydroxide. Coupling of the acid 5 with 3-(chloromethyl)-6-nitroindoline 6 (prepared from the known 1-(tert-butyloxycarbonyl)-3-chloromethyl-6-nitroindoline [see WO 88/04659 and WO 91/16324] gave the nitro-seco-CI analogue 7 (an example of formula (I) where X is Cl, Y is NO₂ and Ht is 4-butyramido-1-methyl-2-pyrrolecarboxamido.

In Scheme 2, coupling of methyl trans-3-aminocinnamate 9 and 1-methylpyrrole-2-carboxylic acid with EDCI.HCl in pyridine gave the ester 10, which was hydrolysed to the acid 11 with Cs₂CO₃ in aqueous MeOH. Coupling of the acid 11 with 3-chloro-methyl-6-nitroindoline 6 gave 1-[(E) -3-(1-methylpyrrole-2-carboxamido)cinnamoyl] -3-chloromethyl-6-nitroindoline (12) (an example of formula I where X is Cl, Y is NO₂ and Ht is (E)-3-(1-methylpyrrole-2-carboxamido)cinnamoyl.

C. GDEPT

C(i)-Vector Systems

In general, the vector for use in GDEPT therapies may be any suitable DNA or RNA vector.

Suitable viral vectors include those which are based upon a retrovirus. Such vectors are widely available in the art. Huber et al (ibid) report the use of amphotropic retroviruses for the transformation of hepatoma, breast, colon or skin cells. Culver et al (Science (1992) 256; 1550–1552) also describe the use of retroviral vectors in GDEPT. Such vectors or vectors derived from them may also be used. Other retroviruses may also be used to make vectors suitable for use in the present invention. Such retroviruses include rous sarcoma virus (RSV).

Englehardt et al (Nature Genetics (1993) 4; 27–34) describe the use of adenovirus based vectors in the delivery of the cystic fibrosis transmembrane conductance product (CFTR) into cells, and such adenovirus based vectors may also be used. Vectors utilising adenovirus promoter and other control sequences may be of use in delivering a system according to the invention to cells in the lung, and hence useful in treating lung tumours.

Other vector systems including vectors based on the Molony murine leukaemia virus are known (Ram, Z et al, Cancer Research (1993) 53; 83–88; Dalton & Treisman, Cell (1992) 68; 597–612). These vectors contain the Murine Leukaemia virus (MLV) enhancer cloned upstream at a β-globin minimal promoter. The β-globin 5' untranslated region up to the initiation ATG is supplied to direct efficient translation of the enzyme.

Suitable promoters which may be used in vectors described above, include MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

C(ii)-Nitroreductase

Compounds of the formula (I) in which Y is NO₂, N(O)RR, or a group of formula (II) can be activated by reduction of this group by nitroreductase.

Preferably, the enzyme is a non-mammalian nitroreductase enzyme, such as a bacterial nitroreductase. An *E. coli* nitroreductase as disclosed in WO93/08288 is particularly preferred. The enzyme may be modified by standard recombinant DNA techniques, e.g. by cloning the enzyme, determining its gene sequence and altering the gene sequence by methods such as truncation, substitution, deletion or insertion of sequences for example by site-directed mutagenesis. Reference may be made to "Molecular Cloning" by Sambrook et al (1989, Cold Spring Harbor) for discussion of standard recombinant DNA techniques. The modification made may be any which still leaves the enzyme with the ability to reduce the nitro group in formula I or II but alters other properties of the enzyme, for example its rate of reaction or selectivity.

In addition, small truncations in the N-and/or C-terminal sequence may occur as a result of the manipulations required to produce a vector in which a nucleic acid sequence encoding the enzyme is linked to the various other vector sequences.

D. ADEPT

For applications in ADEPT systems, an antibody directed against a tumour specific marker is linked to the nitroreductase enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')₂ fragments, as well as single chain antibodies. Furthermore, the antibodies and fragments thereof may be humanised antibodies, e.g. as described in EP-A-239400.

The antibodies may be produced by conventional hybridoma techniques or, in the case of modified antibodies or fragments, by recombinant DNA technology, eg by the expression in a suitable host vector of a DNA construct encoding the modified antibody or fragment operably linked to a promoter. Suitable host cells include bacterial (eg. *E. coli*), yeast, insect and mammalian. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

E. Physioloqically Functional Derivatives

Physiologically functional derivatives of prodrugs include salts, amides and esters. Esters include carboxylic acid esters in which the non-carbonyl moiety of the ester grouping is selected from straight or branched chain $C_{1-6}$alkyl, (methyl, n-propyl, n-butyl or t-butyl); or $C_{3-6}$ cyclic alkyl (e.g. cyclohexyl). Salts include physiologically acceptable base salts, eg derived from an appropriate base, such as alkali metal (e.g. sodium), alkaline earth metal (e.g. magnesium) salts, ammonium and $NR''_4$ (wherein R'' is $C_{1-4}$ alkyl) salts. Other salts include acid addition salts, including the hydrochloride and acetate salts. Amides include non-substituted and mono-and di-substituted derivatives. Such derivatives may be prepared by techniques known per se in the art of pharmacy.

F. Applications of the Invention

Compounds of the invention can be used in vitro or in vivo for a range of applications. For example, a number of vector systems for the expression of nitroreductase in a cell have been developed. The further development of such systems (e.g. the development of promoters suitable for specific cell types) requires suitable candidate prodrugs capable of killing cells when activated by nitroreductase. Prodrug compounds of the present invention may be used in such model systems. The model systems may be in vitro model systems or xenograft model systems comprising for example human tumour cells implanted in nude mice.

Compounds of the invention which are not activatable by an enzyme may be tested in vitro against panels of different tumour cells types to determine efficacy against such tumour cells. The efficacy of compounds of the invention against a range of tumour cell types may be used as points of reference for the development of further antitumour compounds. Compounds of the present invention may also be tested in combination with additional anti-cancer compounds to determine potential combination drug systems, for example combinations which are synergistic.

The compounds of the invention may also be used in a method of treatment of the human or animal body. Such treatment includes a method of treating the growth of neoplastic cells in a patient with neoplastic disease which comprises administering to a patient in need of treatment compounds of formula (I) of the invention, or compounds of formula (II) of the invention as part of an ADEPT or GDEPT therapy system. Neoplastic diseases include leukaemia and solid tumours such as breast, bowel and lung tumours including small cell lung carcinoma.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

Compounds of the formula (I) of the present invention in which Y is not a group of formula (II) may be used in a method of treatment of neoplastic disease in a patient, which method comprises administering to a patient in need of treatment an effective amount of a compound of formula (I). The compound may be administered in the form of a pharmaceutical composition.

While the exact dose of the compound will be at the discretion of the physician, taking account of the condition and needs of the patient, typical doses will be in the range of from about 0.1 to 200 mg/Kg, preferably about from 10 to 100 mg/Kg per patient per day.

P(i):ADEPT Therapy

The antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour the premature release of the compound of formula (II) is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the such part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922. A suitable dose of conjugate may be from 500 to 200,000 enzyme units/m$^2$ (e.g. 20,000 enzyme units/m$^2$) and a suitable dose of prodrug may be from about 0.1 to 200 mg/Kg, preferably about from 10 to 100 mg/Kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The ADEPT system when used with nitroreductase also preferably comprises a suitable cofactor for the enzyme. Suitable cofactors include a riboside or ribotide of nicotinic acid or nicotinamide.

The antibody/enzyme conjugate may be administered by any suitable route usually used in ADEPT therapy. This includes parenteral administration of the antibody in a manner and in formulations similar to that described in section F(iv) below.

F(ii): GDEPT Therapy

For use of the vectors in therapy, the vectors will usually be packaged into viral particles and the particles delivered to the site of the tumour, as described in for example Ram et al (ibid). The viral particles may be modified to include an antibody, fragment thereof (including a single chain) or tumour-directed ligand to enhance targeting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. Viruses, for example isolated from packaging cell lines may also be administered by regional perfusion or direct intratumoral direction, or direct injection into a body cavity (intracaviterial administration), for example by intra-peritoneum injection.

The exact dosage regime for GDEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of modified virus and administration by the intravenous route is frequently found to be the most practical.

In GDEPT systems the amount of virus or other vector delivered will be such as to provide a similar cellular concentration of enzyme as in the ADEPT system mentioned above. Typically, the vector will be administered to the patient and then the uptake of the vector by transfected or infected (in the case of viral vectors) cells monitored, for example by recovery and analysis of a biopsy sample of targeted tissue. This may be determined by clinical trials which involve administering a range of trial doses to a patient and measuring the degree of infection or transfection of a target cell or tumour. The amount of prodrug required will be similar to or greater than that for ADEPT systems.

In using a GDEPT system the prodrug will usually be administered following administration of the vector encoding an enzyme. Suitable doses of prodrug are from about 0.1 to 200 mg/Kg, preferably about from 10 to 100 mg/Kg per patient per day.

F(iii): Administration of Drug or Prodrug

While it is possible for the compounds of formula (I) or the prodrugs of where Y is a group formula (II) to be administered alone it is preferable to present them as pharmaceutical formulations. The formulations comprise the compounds, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy) propyl]-N,N,N-triethylammonium (DOTMA), those comprising dioleoylphosphatidylethanolamine (DOPE), and those comprising 3β[N-(n'N'-dimethylaminoethane)-carbamoyllcholesterol (DC-Chol).

Formulations suitable for parenteral or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, eg. at daily, weekly or monthly intervals, or in response to a specific need of a patient. Preferred routes of administration are oral delivery and injection, typically parenteral or intramuscular injection or intratumoural injection.

The exact dosage regime will, of course, need to be determined by individual clinicians for individual patients and this, in turn, will be controlled by the exact nature of compound of formula (I) but some general guidance can be given. Typical dosage ranges generally will be those described above which may be administered in single or multiple doses. Other doses may be used according to the condition of the patient and other factors at the discretion of the physician.

The following Examples illustrate the invention.

EXAMPLE 1.

Preparation of 1-(E)-4-butyramido-1-methyl-2-pyrroleacryloyl)-3-(chloromethyl)-6-nitroindoline (7), 6-amino-1-[(E)-4-butyramido-1-methyl-2-pyrroleacryloyl]-3-(chloromethyl)indoline (8) and 1-[(E)-4-butyramido-1-methyl-2-pyrroleacryloyl]-3-(chloromethyl)-6-[(4-nitrobenzyl)carbonyl]-aminoindoline (8a) by the Method of Scheme 1.

A mixture of 1-methyl-4-nitro-2-pyrrolecarboxaldehyde (1) [P. Fournari, *Bull. Soc. Chem. Fr.* 1963, 488–491] (0.24 g, 1.56 mmol), methyl triphenylphosphorylidene acetate (0.57 g, 1.71 mmol) and benzene (25 mL) was heated under reflux for 24 h. Purification by dry flash column chromatography, eluting with a gradient of 0–5% $Et_2O$ in $CH_2Cl_2$, gave (E)-methyl 1-methyl-4-nitro-2-pyrroleacrylate (2) as a bright yellow solid (0.33 g, 100%) mp 146–147° C. $^1H$ NMR $(CDCl_3)\delta7.55$ (d, J=1.8 Hz, 1 H, H-5), 7.47 (d, J=15.8 Hz, 1 H, H-β), 7.07 (d, J=1.8 Hz, 1 H, H-3), 6.27 (d, J=15.8 Hz, 1 H, H-α), 3.77, 3.75 (2×s, 3 H each, $CO_2CH_3$, $NCH_3$). $^{13}C$ NMR δ166.9 ($CO_2$), 136.6, 129.7 (C-2, 4), 130.3, 125.4 (C-3, 5), 117.8, 106.0 (CH=CH), 51.8 ($CO_2CH_3$), 35.3 ($NCH_3$). Anal. Calculated for $C_9H_{10}N_2O_4$: C, 51.4; H, 4.8; N, 13.3. Found: C, 51.4; H, 4.7; N, 13.3%.

Alternatively, a solution of 1 (0.20 g, 1.30 mmol), malonic acid (0.68 g, 6.5 mmol) and piperidine (2 drops) in pyridine (2 mL) was stirred at room temperature at for 20 h and at 100° C. for 4 h, then 30% aqueous $H_2SO_4$ (10 mL) was added. The precipitate that formed was removed by filtration and washed with water to give (E)-1-methyl-4-nitro-2-pyrroleacrylic acid (2) as fine yellow needles (0.23 g, 92%). $^1H$ NMR $[(CD_3)_2SO]$ δ12.35 (br s, 1 H, $CO_2H$), 8.13 (d, J=1.9 Hz, 1 H, H-5), 7.44 (d, J=15.9 Hz, 1 H, H-β), 7.41 (d, J=1.9 Hz, 1 H, H-3), 6.46 (d, J=15.9 Hz, 1 H, H-α), 3.79 (s, 3 H, $NCH_3$). $^{13}C$ NMR δ167.4 ($CO_2H$), 135.3, 129.9 (C-2, 4), 130.6, 127.0, 118.6, 105.8 (C-3, 5, α, β), 34.8 ($NCH_3$). Anal. Calculated for $C_8H_8N_2O_4$: C, 49.0; H, 4.1; N, 14.3. Found: C, 49.0; H, 4.0; N, 14.1%.

Dimethyl sulfate (0.12 mL) was added to a solution of 3 (0.10 g, 0.51 mmol) and $NaHCO_3$ (0.10 g, 0.61 mmol) in methanol-water (5:1, 12 mL) at reflux, and heating continued for 1 h. The mixture was diluted with water (50 mL) and extracted with EtOAc (3×25 mL). The combined extracts were washed with water (2×50 mL), dried (brine, $MgSO_4$) and evaporated. The residue was purified by dry-flash column chromatography, eluting with 0–5% $Et_2O$ in $CH_2Cl_2$, to give 2 (63 mg, 59%).

A refluxing solution of 2 (50 mg, 0.24 mmol) in aqueous MeOH (1:12.5, 5.4 mL) was treated with iron powder (70 mg, 1.25 mmol) and butyric anhydride (0.40 mL, 2.45 mmol). After 30 min further butyric anhydride (0.10 mL, 0.61 mmol) was added, and 45 min after the addition of the iron, the mixture was allowed to cool and the solids were removed by filtration and washed with MeOH and water. The combined filtrates were diluted with water (25 mL) and extracted with EtOAc (3×25 mL). The combined extracts were washed sequentially with water, saturated aqueous $NaHCO_3$, water, and brine, then dried ($MgSO_4$) and evaporated. Dry-flash column chromatography, eluting with a gradient of 0–50% EtOAc in $CH_2Cl_2$, gave (E)-methyl 4-butyramido-1-methyl-2-pyrroleacrylate (4) (45 mg, 75%) as cream plates, mp 109–101°0 C. $^1H$ NMR $(CDCl_3)$ δ8.0–7.4 (mobile br s, 1 H, NH), 7.51 (d, J=15.6 Hz, 1 H, H-β), 7.31 (d, J=1.8 Hz, 1 H, H-5), 6.39 (d, J=1.8 Hz, 1 H, H-3), 6.03 (d, J=15.6 Hz, 1 H, H-α), 3.72, 3.62 (2×s, 3 H each, $CO_2CH_3$, $NCH_3$), 2.27 (t, J=7.4 Hz, 2 H, $CH_2CH_2CH_3$), 1.71 (sx, J=7.4 Hz, 2 H, $CH_2CH_2CH_3$), 0.96 (t, J=7.4 Hz, 3 H, $CH_2CH_2CH_3$). $^{13}C$ NMR δ170.3, 168.1 (NHCO, $CO_2$), 131.9, 118.5, 112.5, 102.0 (C-3, 5, α, β), 126.7, 123.5 (C-2, 4), 51.5 ($CO_2CH_3$), 38.8 ($NCH_3$), 34.2 ($CH_2CH_2CH_3$), 19.1 ($CH_2CH_2CH_3$), 13.7 ($CH_2CH_2CH_3$). Anal. Calculated for $C_{13}H_{18}N_2O_3$: C, 62.4; H, 7.3; N, 11.2. Found: C, 62.1; H, 7.6; N, 11.0%.

A solution of 4 (0.167 g, 0.667 mmol) and 0.2 M aqueous NaOH (5.7 mL, 1.13 mmol) in MeOH (10 mL) was heated under reflux for 50 min. The mixture was cooled to 0° C., 2 M aqueous HCl (0.67 mL, 1.33 mmol) was added, and the mixture was poured onto ice (50 g). The precipitate that formed was collected by filtration and washed with water to give (E)-4-butyramido-1-methyl-2-pyrroleacrylic acid (5) as yellow needles (0.133 g, 85%) mp 74–76° C. (dec.) and 165–166° C. (with evolution of gas). $^1H$ NMR $[(CD_3)_2SO]$ δ12.02 (br s, 1 H, $CO_2H$), 9.76 (br s, 1 H, CONH), 7.44 (d, J=15.6 Hz, 1 H, H-β), 7.27 (d, J=1.6 Hz, 1 H, H-5), 6.53 (d, J=1.6 Hz, 1 H, H-3), 6.02 (d, J=15.6 Hz, 1 H, H-α), 3.66 (s, 3 H, $NCH_3$), 2.19 (t, J=7.3 Hz, 2 H, $CH_2CH_2CH_3$), 1.57 (sx, J=7.3 Hz, 2 H, $CH_2CH_2CH_3$), 0.88 (t, J=7.3 Hz, 3 H, $CH_2CH_2CH_3$). $^{13}C$ NMR δ169.2, 168.0 (NHCO, $CO_2$), 131.9, 117.8, 113.6, 101.9 (C-3, 5, α, β), 125.8, 124.2 (C-2, 4), 37.5 ($CH_2CH_2CH_3$), 33.6 ($NCH_3$), 18.7 ($CH_2CH_2CH_3$), 13.6 ($CH_2CH_2CH_3$) Anal. Calculated for $C_{12}H_{16}N_2O_4$: C, 61.0; H, 6.8; N, 11.9. Found: C, C, 60.8; H, 8.4; N, 11.7%.

A mixture of 5 (37 mg, 0.16 mmol), 3-(chloromethyl)-6-nitroindoline (6) [prepared by in situ acid hydrolysis of 1-(tert-butyloxycarbonyl)-3-chloromethyl-6-nitroindoline] [for preparation see WO 88/04659 and WO 91/19624](34 mg, 0.16 mmol), 1-(3-dimethylaminopropyl)-3-ethylcarbodiimide hydrochloride (EDCI, 92 mg, 0.48 mmol) and DMA (5 mL) were stirred at room temperature for 20 h. The mixture was diluted with water (50 mL) and extracted with EtOAc (4×20 mL). The combined extracts were washed with water (3×50 mL) and brine, dried over $MgSO_4$, and evaporated. Dry-flash column chromatography, eluting with a gradient of 0–100% EtOAc in $CH_2Cl_2$, gave 1-(E)-4-butyramido-1-methyl-2-pyrroleacryloyl)-3-(chloromethyl)-6-nitroindoline (7) as a yellow solid (43 mg, 62%). $^1H$ NMR $(CDCl_3)$ δ6 9.09 (br s, 1 H, H-7), 7.94 (dd, J=8.2, 2.2 Hz, 1 H, H-5), 7.77 (d, J=14.9 Hz, 1 H, H-β'), 7.36 (d, J=8.2 Hz, 1 H, H-4), 7.24 (d, J=1.6 Hz, 1 H, H-5'), 7.19 (br s, 1 H, NH), 6.66 (d, J=1.6 Hz, 1 H, H-3'), 6.47 (d, J=14.9 Hz, 1 H, H-α'), 4.46 (d, J=10.7, 9.8 Hz, 1 H, H-2), 4.25 (d, J=10.7, 5.0 Hz, 1 H, H-2), 3.95–3.61 (m, 3 H, $CH_2Cl$, H-3), 3.70 (s, 3 H, $NCH_3$), 2.32 (t, J=7.4 Hz, 2 H, $CH_2CH_2CH_3$), 1.75 (sx, J=7.4 Hz, 2 H, $CH_2CH_2CH_3$), 1.00 (t, J=7.4 Hz, 3 H, $CH_2CH_2CH_3$) .

A solution of 7 (28 mg, 0.065 mmol) and AcOH (0.02 mL, 0.33 mmol) in MeOH (14 mL) and water (2.8 mL) was treated at reflux with iron powder (20 mg, 0.36 mmol). After 20 min, further iron powder (50 mg, 0.90 mmol) and AcOH (0.5 mL, 0.87 mmol) were added, and after an additional 40 min the mixture was poured into dilute aqueous $NaHCO_3$ (100 mL) and extracted with EtOAc (4×20 mL). The combined extracts were washed with dilute aqueous $NaHCO_3$ (2×50 mL), dried (brine, $MgSO_4$), and evaporated. Multiple sweep preparative thin layer chromatography, eluting with EtOAc, gave 6-amino-1-[(E)-4-butyramido-1-methyl-2-pyrroleacryloyl]-3-(chloromethyl)indoline (8) (12 mg, 45%) as a bright yellow solid. $^1H$ NMR $(CDCl_3)$ 7.76 (br s, 1 H, H-7), 7.68 (d, J=14.9 Hz, 1 H, H-β) 7.35 (br s, 1 H, NH), 7.24 (d, J=1.7 Hz, 1 H, H-5'), 6.97 (d, J=8.0 Hz, 1 H, H-4), 6.59 (br s, 1 H, H-3'), 6.49 (br d, J=14.9 Hz, 1 H, H-α), 6.37 (dd, J=8.0, 2.2 Hz, 1 H, H-5), 4.29 (dd, J=8.0, 2.2 Hz, 1 H, H-2), 4.11 (dd, J=10.8, 4.4 Hz, 1 H, H-2), 3.74 (dd, J=10.7, 4.3 Hz, 1 H, CHHCl), 3.64 (s, 3 H. $NCH_3$), 3.71–3.59 (m, 1 H, H-3), 3.49 (dd, J=10.7, 9.7 Hz, 1 H, CHHCl), 2.29 (t, J=7.4H z, 2 H, $CH_2CH_2CH_3$), 1.73 (sx, J=7.4 Hz, 2 H, $CH_2CH_2CH_3$), 0.98 (t, J=7.4 hz, 3 H, $CH_2CH_2CH_3$).

4-Nitrobenzyl chloroformate (52 mg, 0.24 mmol) was added to a solution of 8 (48 mg, 0.12 mmol) in dry pyridine (6 mL) and the yellow solution was stirred at 20° C. More 4-nitrobenzyl chloroformate (52 mg, 0.24 mmol) was added after 30 min. After a further 1 h water was added and the mixture stirred for 30 min until the oil that separated had solidified. The solid was filtered off, washed with water, dried, and triturated with hot EtOAc to give 1-[(E)-4-butyramido-1-methyl-2-pyrroleacryloyl]-3-(chloromethyl)-6-[(4-nitrobenzyloxy)carbonyl]aminoindoline (8a) (49 mg, 71%) as a yellow solid, mp 207–209.5° C. $^1$H NMR [(CD$_3$)$_2$SO] δ6 9.91 (s, 1 H, NH), 9.76 (s, 1 H, NH), 8.40 (s, 1 H, H-7), 8.27 (d, J=8.7 Hz, 2 H, ArHo to NO$_2$), 7.70 (d, J=8.7 Hz, 2 H, ArHm to NO$_2$), 7.54 (d, J=15.0 Hz, 1 H. H-β) 7.28 (d, J=8.2 Hz, 1 H, H-4), 7.22 (d, J=1.5 Hz, 1 H, H-5'), 7.16 (d, J=8.2 Hz, 1 H, H-6), 6.71 (d, J=1.4 Hz, 1 H. H-3'), 6.64 (d, J=15.0 Hz, 1 H, H-α), 5.30 (s, 2 H, ArCH$_2$O), 4.48–4.39 (m, 1 H, H-2), 4.12 (dd, J=10.5, 4.1 Hz, 1 H, ArCH$_2$O), 4.48–4.39 (m, 1 H, H-2), 4.12 (dd, J=10.5, 4.1 Hz, 1 H, H-2), 3.98–3.92 (m, 1 H, CHCH$_2$Cl), 3.85–3.76 (m, 2 H, CHCH$_2$Cl), 3.68 (s, 3H, NCH$_3$), 2.20 (t, J=7.3 Hz, 2 H, CH$_2$CH$_2$CH$_3$), 1.58 (sx, J=7.4 Hz, 2 H, CH$_2$CH$_2$CH$_3$), 0.89 (t, J=7.4 Hz, 3 H, CH$_2$CH$_2$CH$_3$).

EXAMPLE 2.

Preparation of 1[(E)-3-(1-methylpyrrole-2-carboxamido)cinnamoyl]-3-chloromethyl-6-nitroindoline (12) by the method of Scheme 2.

A mixture of methyl (E)-3-aminocinnamate (9) (1.20 g, 6.77 mmol), 1-methylpyrrole-2-carboxylic acid (0.89 g, 7.11 mmol) and EDCI.HCl (1.56 g, 8.14 mmol) in pyridine (8 mL) was stirred at 50° C. for 2.5 h and then cooled and diluted with water. The precipitated semi-solid was dissolved in CH$_2$Cl$_2$, the solution was washed with 0.5 N HCl (2×) and water (2×) and then dried and concentrated under reduced pressure below 30° C. The residue was chromatographed on silica gel, eluting with CH2Cl2/EtOAc (10:1), to yield a solid which was triturated with i-Pr$_2$O/petroleum ether to give thermally unstable methyl (E) -3-(l-methylpyrrole-2-carboxamido)cinnamate (10) (1.42 g, 74%), mp 89–90° C. $^1$H NMR [(CD$_3$)$_2$SO] δ9.83 (s, 1 H, NH), 8.01 (d, J=1.4 Hz, 1 H, H-2), 7.76 (dt, J=7.8, 1.4 Hz, 1 H, H-4), 7.63 (d, J=16.0 Hz, 1 H, PhCH═CH), 7.45–7.35 (m, 2 H, H-5,6), 7.05 (dd, J=4.0, 1.7 Hz, 1 H, H-pyrrole), 7.03 (t, J=2.0 Hz, 1 H, H-pyrrole), 6.54 (d, J=16.0 Hz, 1 H, Ph CH═CH), 6.11 (dd, J=3.8, 2.6 Hz, 1 H, H-pyrrole), 3.89 (s, 3 H, NCH$_3$), 3.74 (s, 3 H, CO$_2$CH$_3$).

A solution of Cs$_2$CO$_3$ (3.26 g) in H$_2$O (2 mL) was diluted with MeOH (8 mL) and ester 10 (0.91 g, 3.2 mmol) was added. The mixture was heated under reflux for 2.5 h then cooled and acidified with 0.5N HCl. The precipitated solid was collected, dried and dissolved in warm EtOAc. The solution was concentrated to a small volume under reduced pressure below 40° C. and then diluted with i-Pr$_2$O to provide (E) -3- (1-methylpyrrole-2-carboxamido)cinnamic acid (11) (0.79 g, 91%) mp 202–204° C. $^1$H NMR [(CD$_3$)$_2$SO] δ12.44 (br s, 1 H, CO$_2$H), 9.82 (s, 1 H, NH), 7.99 (s, 1 H, H-2), 7.79–7.73 (m, 1 H, H-4), 7.56 (d, J=16.0 Hz, 1 H, PhCH═CH), 7.40–7.34 (m, 2 H, H-5,6), 7.05 (dd, J=4.0, 1.7 Hz, 1 H, H-pyrrole), 7.02 (t, J=2.0 Hz, 1 H, H-pyrrole), 6.44 (d, J=16.0 Hz, 1 H, PhCH═CH), 6.11 (dd, J=3.8,2.6 Hz, 1 H, H-pyrrole), 3.89 (s, 3 H, NCH$_3$).

1-(tert-Butyloxycarbonyl)-3-chloromethyl-6-nitroindole (156 mg, 0.50 mmol) was stirred in HCl-saturated dioxane (5 mL) at 20° C. for 2 h, and the mixture was then evaporated to dryness under high vacuum below 25° C. to give crude 3-chloromethyl-6-nitroindoline (6). Acid 11 (135 mg, 0.50 mmol), EDCI.HCl (240 mg, 1.25 mmol) and DMA (1.5 mL) were then added in sequential fashion and the mixture was stirred at 20° C. for 2 h. Dilution with water provided the crude product which was recrystallised twice from EtOAc to give 1-[(E)-3-(1-methylpyrrole-2-carboxamido)-cinnamoyl]-3-chloromethyl-6-nitroindole (12) (166 mg, 72%), mp 215° C. $^1$H NMR [(CD$_3$)$_2$SO] δ9.86 (s, 1 H, NH), 8.97 (s, 1 H, H-7), 8.03–7.96 (m, 1 H, H-5), 8.00 (s, 1 H, H-2'), 7.80 (d, J=8.0 Hz, 1 H, H-4'), 7.70 (d, J=8.3 Hz, 1 H, H-4), 7.69 (d, J=15.4 Hz, 1 H, PhCH═CH), 7.54 (d, J=7.4 Hz, 1 H, H-6'), 7.41 (t, J=7.9 Hz, 1 H, H-5'), 7.11 (d, J=15.4 Hz, 1 H, PhCH═CH), 7.1–7.04 (m, 2 H, H-pyrrole), 6.12 (t, J=3.1 Hz, 1 H, H-pyrrole), 4.66 (t, J=10.0 Hz, 1 H, H-2), 4.34 (dd, J=10.6, 5.1 Hz, 1 H, H-2), 4.15–3.99 (m, 3 H, H-3, CH$_2$Cl ), 3.90 (s, 3 H, NCH$_3$).

EXAMPLE 3.

Preparation of 1-[(E)-3-(acetylamino) cinnamoyl]-3-chloromethyl-6-nitroindoline by the method of Scheme 2.

Similar reaction of (E)-3-(acetylamino)cinnamic acid and crude 3-chloromethyl-6-nitroindoline (6) (prepared as in Example 2) gave a crude product which was recrystallised from DMF/MeOH/H$_2$O to give 1-[(E)-3-(acetylamino) cinnamoyl]-3-chloromethyl-6-nitroindoline (13) (80%), mp 229–230° C. $^1$H NMR [(CD$_3$)$_2$SO] δ10.06 (s, 1 H, NH), 8.97 (s, 1 H, H-7), 7.99 (dd, J=8.3, 2.3 Hz, 1 H, H-5), 7.86 (s, 1 H, H-2), 7.73–7.61 (m, 2 H, H-4,4'), 7.66 (d, J=15.3 Hz, 1 H, PhCH═CH), 7.53 (d, J=7.8 Hz, 1 H, H-6), 7.38 (t, J=7.9 Hz, 1 H, H-5), 7.08 (d, J=15.4 Hz, 1 H, PhCH═CH), 4.65 (t, J 10.0 Hz, 1 H, H-2), 4.33 (dd, J=10.7, 5.2 Hz, 1 H, H-2), 4.14–4.00 (m, 3 H, H-3, CH$_2$Cl ), 2.07 (s, 3 H, CH$_3$).

EXAMPLE 4.

Biological Activity

The compounds of Formula I show cytotoxicity to mammalian tumour cells, and are thus of interest as anticancer drugs. The compounds of formula I in which Y is NO$_2$ or a group of formula II also show high levels of activation by the isolated E. coli NR2 nitroreductase enzyme.

To evaluate the activity of a compound UV4 cells were maintained in exponential phase growth (doubling times 14 and 15 h respectively) using Alpha MEM containing fetal calf serum (10% v/v) without antibiotics, and were subcultured twice weekly by trypsinization. Bulk cultures were prepared for experiments by seeding cells in spinner flasks at 10$^4$ cells/mL in the above medium with addition of penicillin (100 IU/mL) and streptomycin (100 μg/mL). Cultures were initiated in 96-well microtiter trays to give 200 (AA8) or 300 (UV4) cells in 0.05 mL per well. After growth in a CO$_2$ incubator for 24 h, drugs were added in culture medium, using serial two-fold dilutions to provide duplicate cultures at five different concentrations for each of eight drugs (plus eight controls) per tray. After 18 h drugs were removed by washing cultures three times with fresh medium, and the trays were incubated for a further 78 h. Cell density was then determined by staining with methylene blue as described [Finlay, G. J.; Baguley, B. C.; Wilson, W. R. Anal. Biochem., 1984, 139: 272–277]. The IC$_{50}$ was calculated as the drug concentration providing 50% inhibition of growth relative to the controls.

To evaluate the activation of the compound by E. coli nitroreductase 2 (NR2) the experiment was repeated but in addition purified E. coli nitroreductase enzyme (1 μg/mL) and NADH (1 mM, as cofactor) was added during the entire time of the incubation. As a comparison the experiment was also repeated but with the addition only of NADH and not NR2.

The results are shown in Table 1 below. Where multiple determinations were carried out the IC$_{50}$ is given as an average ±SEM. Where one determination only was carried out a single $IC_{50}$ value is given.

TABLE 1

| Compound (see Schemes) | $IC_{50}$ (nM) drug alone | $IC_{50}$ (nM) drug + NADH | $IC_{50}$ (nM) drug + NADH + NR2 | Ratio* |
|---|---|---|---|---|
| 7 | 2940 ± 320 | 1080 ± 340 | 43 ± 4 | 70 ± 13 |
| 8 | 38 | 24 | 35 | 1.1 |
| 12 | ca. 5000 | | | ca. 30 |
| 13 | 335 | 339 | 74 ± 23 | 3.5 |

*$IC_{50}$ drug alone/$IC_{50}$ drug + NADH + NR2. Values are intraexperiment ratios.

What is claimed is:

1. A compound which is a 6-substituted indoline of the formula (I):

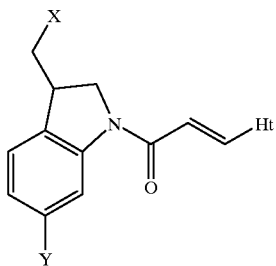

wherein:
X is halogen or $OSO_2R$;
Y is $NO_2$, $N_3$, NHOH, NHR, NRR, $N=NR_A$, N(O)RR, SR or $SSR_A$, where $R_A$ represents R or another moiety of formula (I);
or Y is a group of formula:

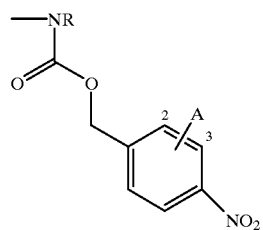

where A may be a group CONHR, NHCOR or OR at any one of positions 2 or 3;

Ht is a 5 or 6 membered carbocycle or heterocycle containing up to two atoms selected from N, O or S, the carbocycle or heterocycle being optionally substituted by a group Q wherein either Q is one or two of H, OR or NRR, which may be the same or different when Q is two, or Q is a group $CONHJ^1$, $NHCOOJ^1$, $NHCOOJ^1$ or $NHCONHJ^1$ where $J^1$ is either a group R or a 5 or 6 membered carbocycle or heterocycle containing up to two atoms selected from N, O or S and can bear a substituent R, OR, NHCOR, NHCOOR or NHCONHR;

wherein if Ht is a pyrrol-2-yl group, then the pyrrolyl group may bear an N-methyl group;

where R represents H or $C_{1-5}$ alkyl optionally substituted with from 1 to 4 hydroxyl, acid (COOH) or amino groups which amino may be optionally substituted by one or two $C_{1-5}$ alkyl groups;

or a physiologically thereof.

2. The compound of claim 1, in which Y is $NO_2$ or a group of formula II.

3. The compound of claim 1, wherein X is Cl.

4. The compound of claim 1, in which Ht is phenyl or pyrrolyl.

5. The compound of claim 1, wherein Q is NHCOR, where R is $C_{1-4}$ alkyl or $NHCOJ^1$ where $J^1$ is an optionally substituted 5-or 6-membered heterocycle.

6. The compound of claim 5, in which $J^1$ is pyrrol-2-yl, optionally substituted on the nitrogen atom by $C_{1-4}$ alkyl.

7. 1-(E)4-butyramido-1-methyl-2-pyrroleacryloyl)-3-(chloromethyl)-6-nitroindoline.

8. 6-amino-1[(E)-4-butyramido-1-methyl-2-pyrroleacryloyl]3-(chloromethyl) indoline.

9. 1[(E)-4-butyramido-1-methyl-2pyrroleacryloyly]-3-(chloromethyl)-6[(4-nitrobenzyloxy)carbonyl]-aminoindoline.

10. 1-(E)-3-(1-methylpyrrole-2-carboxamido)cinnamoyl]-3-chloromethyl-6-nitroindoline.

11. A composition comprising: the compound of claim 1; together with a pharmaceutically acceptable carrier or diluent.

12. The composition of claim 11, whereby in said compound Y is $NO_2$, N(O)RR, or a moiety of formula II.

13. A method of treating neoplastic disease, the method comprising:
administering to a patient in need of treatment an effective amount of a compound according to claim 1.

14. The method of claim 13, whereby in said compound Y is $NO_2$, N(O)RR, or a moiety of formula II.

* * * * *

UNITED STATES PATENT AND TRADEMARK OFFICE
CERTIFICATE OF CORRECTION

PATENT NO. : 6,251,933 B1
DATED : June 26, 2001
INVENTOR(S) : Denny et al.

It is certified that error appears in the above-identified patent and that said Letters Patent is hereby corrected as shown below:

Column 17,
Line 19, after the word "physiologically" and before "thereof." please add the following information:
-- acceptable salt, amide, or ester --

Signed and Sealed this

Twenty-fifth Day of January, 2005

JON W. DUDAS
*Director of the United States Patent and Trademark Office*